US005204446A

United States Patent [19]

Kumazawa et al.

[11] Patent Number: 5,204,446

[45] Date of Patent: Apr. 20, 1993

[54] POLYPEPTIDE HAVING IMMUNOREACTIVITY WITH ANTIBODY SPECIFIC TO HEPATITIS B VIRUS

[75] Inventors: Toshiaki Kumazawa; Masatoshi Osanai, both of Hachioji, Japan

[73] Assignee: Olympus Optical Co., Ltd., Tokyo, Japan

[21] Appl. No.: 503,239

[22] Filed: Apr. 2, 1990

[30] Foreign Application Priority Data

Apr. 14, 1989 [JP] Japan .................................. 1-95015

[51] Int. Cl.[5] ..................... A61K 37/00; A61K 37/02; C07K 5/00; C07K 7/00

[52] U.S. Cl. .................................... 530/325; 530/324; 530/329; 514/12; 514/13; 514/17

[58] Field of Search ........................ 530/325, 324, 329; 514/12, 13, 17

[56] References Cited

PUBLICATIONS

Unger et al., Embo J., vol. 9, No. 6, pp. 1889–1895, 1990.
Rutter et al., CA(95):21196v, p. 357, 1981.
Valenzuela et al., Chem Abst., CA94:187080g, p. 184, 1981.
Kumazawa et al., Chem Abstr., CA115:47662a, p. 666, 1991.
Vaudin et al., J. Gen. Virol., 69, pp. 1383–1389, 1988.
Lo et al., Virology, 167, pp. 289–292, 1988.
Immunochemistry, vol. 12, pp. 423–438 (1975), Atassi.
Bull. Chem. Soc., Jpn, vol. 40, pp. 2164–2167 (1967).
Clinical Science, "A 'New' Antigen in Leukemia Sera", vol. 191, No. 7, pp. 541–546 (1965).
Prince, et al., Proc. Natl. Acad. Sci. USA, vol. 79, pp. 579–582 (1982).
Science, vol. 227, pp. 429–433 (1985), "Antibodies to Peptides Detect New Hepatitis B Antigen: . . . ".
Hopp and Woods, Proc. Natl. Acad. Sci. USA, vol. 78, No. 6, pp. 3824–3828 (1981).

*Primary Examiner*—Lester L. Lee
*Assistant Examiner*—A. M. Davenport
*Attorney, Agent, or Firm*—Frishauf, Holtz, Goodman & Woodard

[57] ABSTRACT

A peptide having immunoreactivity with an antibody specific to a hepatitis B virus, containing one of the following amino acid sequences:

(1) Asp-Cys-Val-Phe-Lys-Asp-Trp-Glu-Glu-Leu-Gly-Glu-Glu-Ile-Arg-Leu-Lys-Val-Phe-Val-Leu-Gly-Gly-Cys, (2) Asp-Cys-Val-Phe-Lys-Asp-Trp-Glu-Glu-Leu-Gly-Glu-Glu-Ile-Arg-Leu-Met-Ile-Phe-Val-Leu-Gly-Gly-Cys or (3) Asp-Cys-Leu-Phe-Lys-Asp-Trp-Glu-Glu-Leu-Gly-Glu-Glu-Ile-Arg-Leu-Lys-Val-Phe-Val-Leu-Gly-Gly-Cys.

9 Claims, 5 Drawing Sheets

```
                                        10                                     20
Met-Ala-Ala-Arg-Val-Cys-Cys-Gln-leu-Asp-Pro-Ala-Arg-Asp-Val-Leu-Cys-Leu-Arg-Pro-
                                        30                                     40
Val-Gly-Ala-Glu-Ser-Arg-Gly-Arg-Pro-Val-Ser-Gly-Pro-Phe-Gly-Ala-Leu-Pro-Ser-Pro-
                                        50                                     60
Ser-Pro-Ser-Ala-Val-Pro-Ala-Asp-His-Gly-Ala-His-Leu-Ser-Leu-Arg-Gly-Leu-Pro-Val-
                                        70                                     80
Cys-Ala-Phe-Ser-Ser-Ala-Gly-Pro-Cys-Ala-Leu-Arg-Phe-Thr-Ser-Ala-Arg-Arg-Met-Glu-
                                        90                                    100
Thr-Thr-Val-Asn-Ala-His-Gln-Val-Leu-Pro-Lys-Val-Leu-His-Lys-Arg-Thr-Leu-Gly-Leu-
                                       110                                    120
Ser-Ala-Met-Ser-Thr-Thr-Asp-Leu-Glu-Ala-Tyr-Phe-Lys-Asp-Cys-Val-Phe-Lys-Asp-Tru-
                                       130                                    140
Glu-Glu-Leu-Gly-Glu-Glu-Ile-Arg-Leu-Lys-Val-Phe-Val-Leu-Gly-Gly-Cys-Arg-His-Lys-
                                       150
Leu-Val-Cys-Ala-Pro-Ala-Pro-Cys-Asn-Phe-Phe-Thr-Ser-Ala
```

FIG. 1

POLYPEPTIDE HAVING IMMUNOREACTIVITY WITH ANTIBODY SPECIFIC TO HEPATITIS B VIRUS

BACKGROUND OF THE INVENTION

1. Field of the Invention

The present invention relates to a polypeptide having substantially the same antigenicity as that characteristic of a hepatitis B virus and having immunoreactivity with an antibody to the virus. More specifically, the present invention relates to a polypeptide having an amino acid sequence coinciding with a specific portion of an amino acid sequence coded by an X-gene of the hepatitis B virus.

The polypeptide according to the present invention is effective to detect an antibody specific to the hepatitis B virus. The polypeptide according to the present invention can be used as an immunogen dosed to mammals in order to obtain a polyclonal antibody and a monoclonal antibody for an X-protein, i.e., a protein produced by expression of an X-gene.

2. Description of the Related Art

Carriers of a hepatitis B virus (to be referred to as an HBV hereinafter), i.e., people infected by the HBV have reached two billion, and many of them suffer from the chronic hepatitis. It is known that the HBV carriers or patients of the chronic hepatitis will be finally affected by a liver cirrhosis or hepatocellular carcinoma at a high rate.

Since the HBV was found first in serums of native Australians, it was initially called an Australia antibody (JAMA, vol. 191, pp. 541-546 (1965)). Later, the HBV was found to be a 42-nm diameter spherical particle having a double structure, and this particle is called a Dane particle.

The Dane particle has a core having a diameter of 27 nm, and the core is covered with an envelope portion which is a surface antigen called an HBs antigen. The core contains a nucleocapsid or core antigen (HBc antigen and HBe antigen), an incomplete double-chain HBV-DNA having about 3,200 base pairs, and a DNA polmerase necessary for forming this incomplete double-chain.

In recent years, extensive studies have been made on various HBV-associated markers. As one of these studies, it has been confirmed that detection of antigen and antibody characteristic of the hepatitis B is significantly important for clinical diagnosis.

A synthetic polypeptide having an amino acid sequence corresponding to an antigenic portion contained in a perfect HBs antigen is used in an immunoassay system for detecting an HBs antigen and an anti-HBs antibody (Proc. Natl. Acad. Sci. USA, vol. 79, pp. 579-582 (1982)).

The X-protein is a protein having a molecular weight of about 17 kd and coded by an X-gene located on an HBV-genom. The clinical significance of the X-protein has not yet been clarified. Anne Moriarty et al. reported that an antibody against a synthetic protein corresponding to a part of the X-protein is present in hepatocellular caricinoma patients among the HBV carriers at a high rate (Science, vol. 227, pp. 429-433 (1985)). Since then, a relationship between the expression of HBV X-gene and various diseases associated with the hepatitis B virus has received a great deal of attention.

SUMMARY OF THE INVENTION

It is an object of the present invention to provide a polypeptide used for detecting an X-protein contained in a blood of a chronic hepatitis patient infected by an HBV and an antibody specific to an X-protein (to be referred to as an anti-X antibody hereinafter).

It is another object of the present invention to provide a polypeptide used for diagnosing a hepatocellular carcinoma or the like.

The above objects can be achieved by a polypeptide having immunoreactivity with an antibody specific to a hepatitis B virus, comprising a polypeptide selected from the group consisting of:

(a) a polypeptide represented by an amino acid sequence defined by formula (1):

Asp-Cys-Val-Phe-Lys-Asp-Trp-Glu-Glu-Leu-Gly-
Glu-Glu-Ile-Arg-Leu-Lys-Val-Phe-Val-Leu-Gly-
Gly-Cys (1)

wherein Asp, Arg, Cys, Glu, Gly, Ile, Leu, Lys, Phe, Val, and Trp represent aspartic acid, arginine, cysteine, glutamic acid, glycine, isoleucine, leucine, lysine, phenylalanine, valine, and tryptophan, respectively;

(b) a polypeptide including an amino acid sequence which coincides with a part (containing at least six amino acids) of the sequence of formula (1) and having cross reactivity with the polypeptide defined by formula (1);

(c) a polypeptide which is represented by an amino acid sequence obtained by substituting at least one amino acid of the amino acid sequence defined by formula (1) with other amino acids and which has cross reactivity with the polypeptide defined by formula (1);

(d) a polypeptide which is represented by an amino acid sequence obtained by omitting at least one amino acid from the amino acid sequence defined by formula (1) and which has cross reactivity with the polypeptide defined by formula (1);

(e) a polypeptide which is represented by an amino acid sequence obtained by adding at least one amino acid to the amino acid sequence defined by formula (1) and which has cross reactivity with the polypeptide defined by formula (1); and (f) a polypeptide obtained by bonding at least two of the polypeptides (a) to (e).

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

FIG. 1 is an amino acid sequence of an X-protein coded by an X-gene of an HBV-DNA subtype adr;

DETAILED DESCRIPTION OF THE PREFERRED EMBODIMENTS

Figure 2:
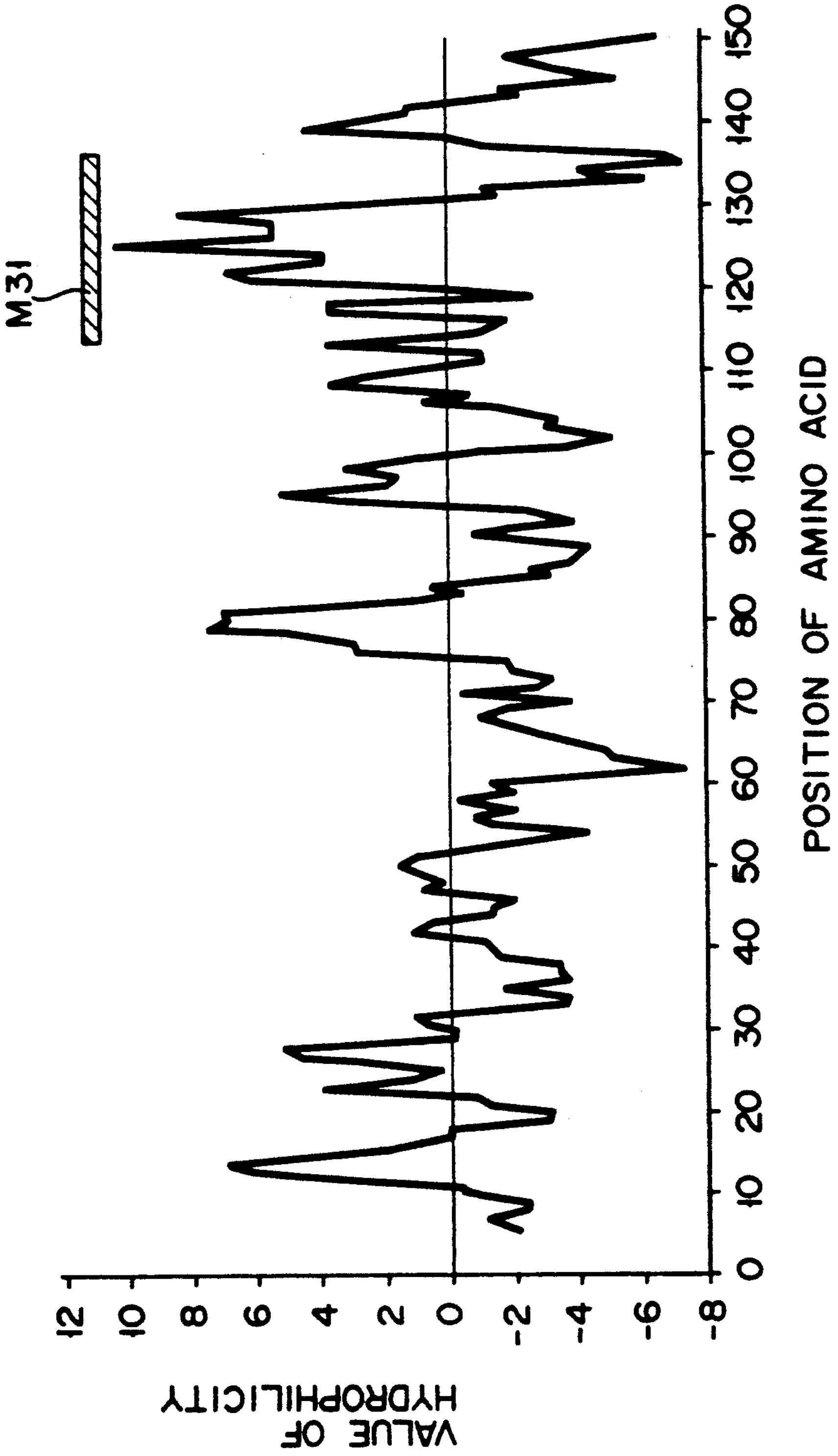
FIG. 2 is a graph showing hydrophilicity values of the respective sites of the X-protein used to predict an antigenic portion of the X-protein.

The present inventors found that an antibody specific to a synthetic peptide having the same amino acid sequence as part of an X-protein were able to serve as a indicator for occurence of hepatocellular carcinoma in an HBV-infected patient.

As shown in FIG. 1, the X-protein coded by the X-gene of the subtype adr is constituted by 154 amino acids. In the specification of the present invention, the left end of the amino acid sequence is an amino terminal, and the right end is a carboxylic terminal.

The present inventors predicted a portion having strong antigenicity in the X-protein based on the hydrophilic values of the respective amino acids in the amino acid sequence in accordance with the method of Hopp and Woods (Proc. Natl. Acad. Sci. USA, Vol. 78, pp. 3824–3828 (1981)). The present inventors synthesized a polypeptide having an amino acid sequence defined by the following formula (1) on the basis of the prediction result described above:

Asp-Cys-Val-Phe-Lys-Asp-Trp-Glu-Glu-Leu-Gly-
Glu-Glu-Ile-Arg-Leu-Lys-Val-Phe-Val-Leu-Gly-
Gly-Cys (1)

wherein

Asp represents aspartic acid
Arg represents arginine
Cys represents cysteine
Glu represents glutamic acid
Gly represents glycine
Ile represents isoleucine
Leu represents leucine
Lys represents lysine
Phe represents phenylalanine
Val represents valine
Trp represents tryptophan The polypeptide having the amino acid sequence defined by formula (1) exhibits antigenicity characteristic of the X-protein. As a result, this polypeptide can specifically immunoreact with an anti-X antibody produced by using the X-protein as an immunogen. An antibody produced by using this polypeptide as an immunogen has specific immunoreactivity with the X-protein. Therefore, the polypeptide having the amino acid sequence defined by formula (1) is a typical example of the polypeptide according to the present invention.

A minimum size of an antigenic determinant is known to be constituted by a sequence of six amino acids (Immunochemistry, 12, pp. 423–438 (1975); Proc. Natl. Acad. Sci. USA, Vol. 78, pp. 3824–3828 (1981)). This indicates that a polypeptide including a sequence of six continuous amino acids in the formula (1) can have the same antigenicity as that of the typical example of the present invention although the polypeptide does not include all the components of the above amino acid sequence. Therefore, any polypeptide including a sequence coinciding with part (i.e., part including at least six amino acids) of the sequence defined by formula (1) is included in the present invention so long as it has cross reactivity with the polypeptide defined by formula (1). Whether a polypeptide has cross reactivity or not is determined by testing immunoreactivity with an anti-HBV antibody.

Because of the same reason as described above, the following polypeptides analogous to the typical example of the polypeptide of the present invention are included in the present invention so long as they have cross reactivity with the typical example. The first analogous polypeptide is a polypeptide obtained by substituting at least one amino acid in the sequence defined by formula (1) with other amino acids. The second analogous polypeptide is a polypeptide obtained by omitting at least one amino acid in the sequence defined by formula (1). The third analogous polypeptide is a polypeptide obtained by adding at least one amino acid to the sequence defined by formula (1).

Specific analogous examples are polypeptides contained in the X-protein coded by X-genes of different subtypes, whose position correspond to that of the polypeptides of formula (1). That is, the polypeptide defined by formula (1) a is part of the X-protein coded by the X-gene of the subtype adr. Therefore, portions (their amino acid sequences are represented by formulas (2) and (3) below) contained in the X-proteins respectively coded by the X-genes of the subtypes adw and ayr, as a part corresponding to formula (1) are the analogous examples. An amino acid or amino acids at underlined portions in formulas (2) and (3) are different from that of formula (1), respectively:

<Subtype adw>

Asp-Cys-Val-Phe-Lys-Asp-Trp-Glu-Glu-Leu-Gly-
Glu-Glu-Ile-Arg-Leu-Met-Ile-Phe-Val-Leu-Gly-
Gly-Cys (2)

<Subtype adw>

Asp-Cys-Leu-Phe-Lys-Asp-Trp-Glu-glu-Leu-Gly-
Glu-Glu-Ile-Arg-Leu-Lys-Val-Phe-Val-Leu-Gly-
Gly-Cys, (3)

The polypeptide according to the present invention is coated on an appropriate support and is used for an immunoassay for detecting an antibody specific to an X-protein. Examples of the appropriate support are a solid-phase support such as a bovine serum albumin (BSA), a polypeptide having a molecular weight of about 50,000 to 100,000, an inner well wall of a synthetic resin microplate, a latex bead having a diameter of about 0.1 μm to 5.0 μm, and a polystyrene bead having a diameter of about 5 mm.

The present invention will be described in detail by way of its examples. These examples only exemplify the present invention but do not limit the scope of the present invention.

EXAMPLE 1

Manufacture of Polypeptide

<Determination of Antigenic Portion of X-Protein>

FIG. 1 shows an amino acid sequence of an X-protein coded by an X-gene of subtype adr contained in an HBV-DNA. An antigenic portion of the X-protein was determined by a method of Hopp and Woods (Proc. Natl. Acad. Sci. USA, Vol. 78, No. 6, pp. 3824–3828 (1981)) on the basis of this amino acid sequence.

Hydrophilicity values inherent to the individual amino acids constituting the above sequence were given, and a sequence (polypeptide-6) consisting of six continuous amino acids was extracted from the above amino acid sequence. The hydrophilic values of the amino acids constituting the polypeptide-6 were added, and the sum is given as a hydrophilicity value representing antigenicity of the polypeptide-6. Hydrophilicity values of 144 polypeptide-6s obtained from the amino acid sequence of FIG. 1 were calculated. The results are shown in FIG. 2. The positions of the polypeptide-6s in the amino acid sequence of FIG. 1 are plotted along the abscissa in FIG. 1. That is, the numeric values along the abscissa represent amino acid positions of the carboxylic terminals of the respective polypeptide-6s in the amino acid sequence of FIG. 1. The hydrophilicity values of the respective polypeptide-6s are plotted along the ordinate in FIG. 1, and antigenicity of each polypeptide-6 is proportional to the corresponding hydrophilicity value.

The polypeptide M31 having amino acid numbers 114 to 137 was selected as a portion predicted to have high antigenicity of the X-protein on the basis of the results in FIG. 2. This polypeptide M31 corresponds to an underlined portion in FIG. 1, and an amino acid sequence of this portion is the same as the sequence defined by formula (1).

<Synthesis of Polypeptide M31>

Synthesis of the polypeptide M31 having the amino acid sequence defined by formula (1) will be described below. This synthesis is not a method using Escherichia coli transformed by a gene recombination technique, but a chemical synthesizing method because chemical synthesis has an advantage in which no limitation as to cutting portions by a restriction enzyme is imposed and a desired amino acid sequence can be freely synthesized.

A polypeptide M31 was obtained by peptide synthesis from symmetric anhydrides of t-butoxycarbonyl amino acids by using a peptide synthesizer 430A (available from Applied Biosystem Corp). This polypeptide M31 was dissolved in anisole dimethylsulfide parathiocresol and was treated for an hour in the presence of a hydrofluoric acid at −5° C. to 0° C. (see Bull. Chem. Soc, Jpn., 40. p. 2164 (1967)).

Figure 3:
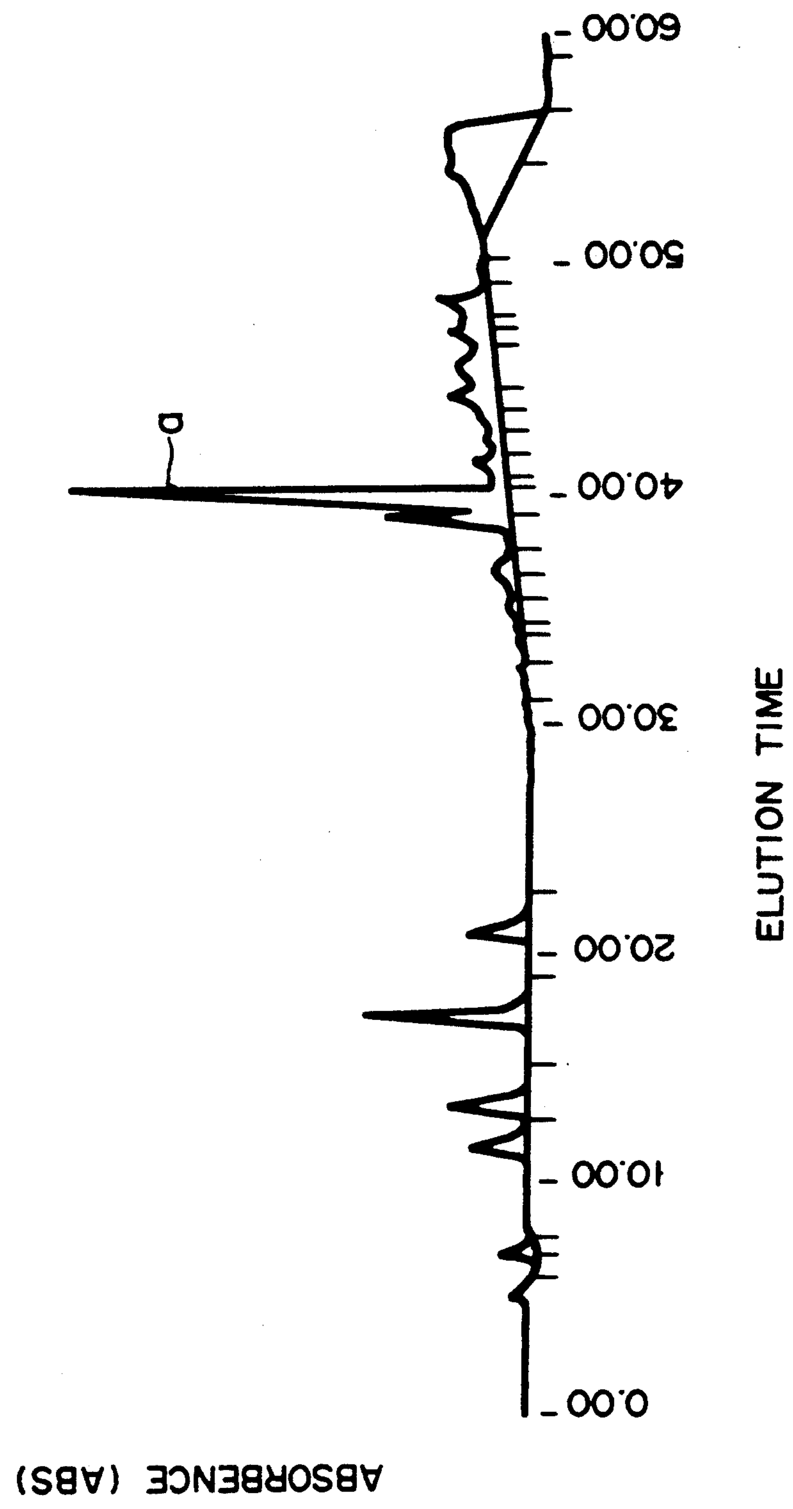
FIGS. 3 and 4 are graphs showing elution patterns obtained by a reversed phase column chromatography used for refining a chemically synthesized polypeptide M31.

The resultant crude crystal was dissolved in 2N acetic acid solution, and extracted thereafter. The extracted crystal was frozen and dried. The dried crystal was filled in and purified by a reversed phase column (ODS-Culumn μ-Bondasphere) available from Waters Corp. filled with 15-μm diameter particles having a functional group C18. In this purification, a solution obtained by dissolving 0.1 wt. % of trifluoroacetic acid (TFA) and 5 wt. % of cyanomethane ($CH_3CN$) in distilled water, and a solution obtained by dissolving 0.1 wt. % of TFA and 50 wt. % of cyanomethane in distilled water were used, and a gradient was obtained at a flow rate of 12 ml/min. An absorbence measurement of a solution flowing out from the column was performed using light having a wavelength of 250 nm. The resultant chromatogram is shown in FIG. 3. The 17th peak a in FIG. 3 corresponds to a polypeptide M31.

Figure 4:
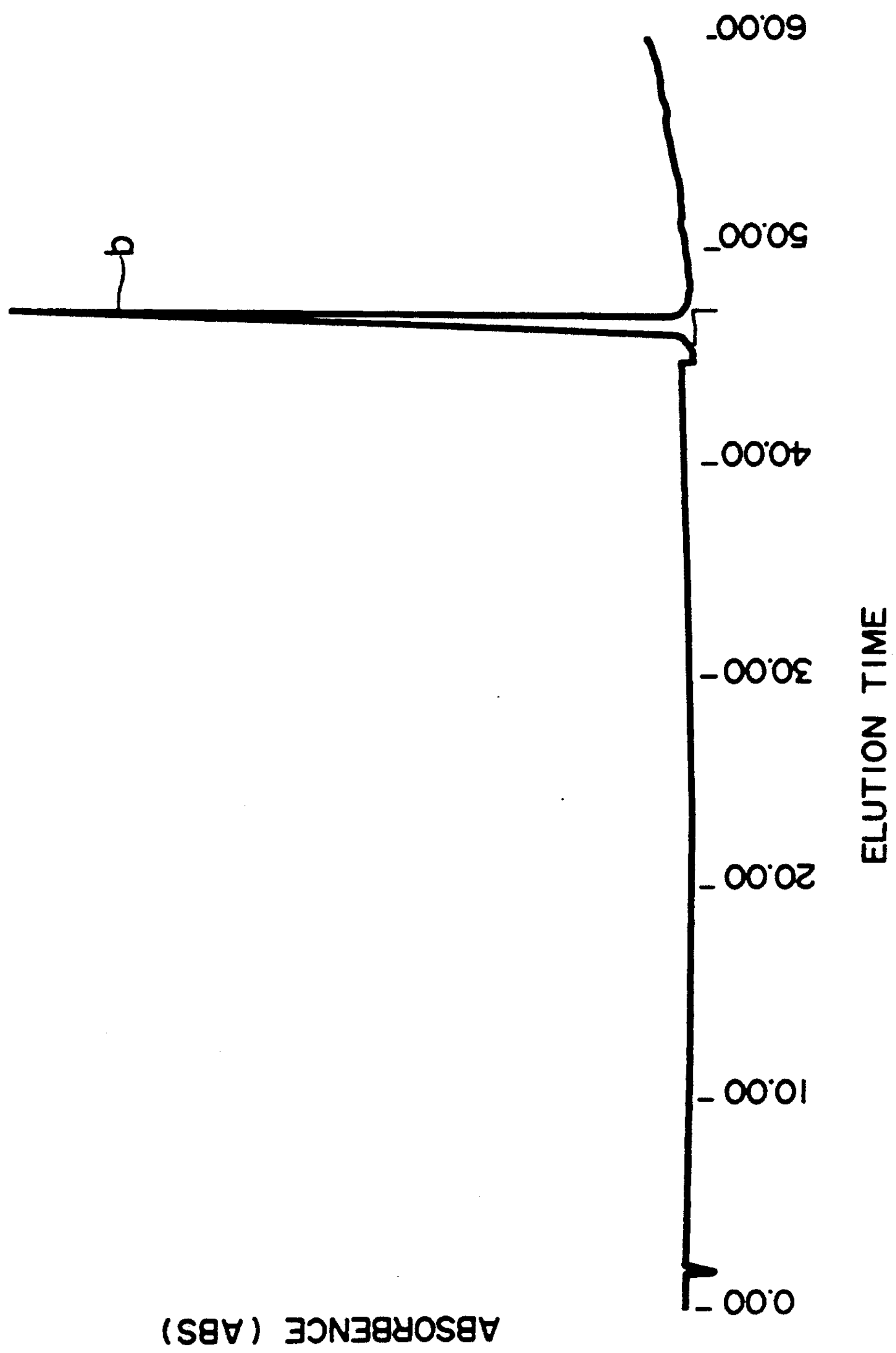

A fraction corresponding to this peak a was applied to the same column again. By using a solvent as in the above experiment, purification was performed with a gradient at a flow rate of 1 ml/min. The resultant chromatogram is shown in FIG. 4. In this case, a wavelength at absorbence measurement was 210 nm. From a fraction corresponding to a peak b in FIG. 4, purified polypeptide M31 was obtained.

EXAMPLE 2

Immobilization of Polypeptide M31 on Support

A solution was prepared by adding 0.04 g/ml of polypeptide M31 to a phosphate buffered saline (PBS) containing 0.15M NaCl and 0.01M $Na_2HPO_4$-$NaH_2PO_4$·2-$H_2O$. This solution was dispensed into each well of ELISA-plate 68667 (available from NUNC Corp.) in an amount of 100 ml/well and was incubated at 37° C. for 60 minutes. The ELISA-plate were washed three times with a 0.01M PBS having a pH of 7.0.

A 0.01M PBS containing 0.1% gelatine was dispensed into each well of ELISA-plate in an amount of 300 μl/well and was incubated at 37° C. for 60 minutes. The ELISA-plate were washed three times with a PBS having a pH of 7.0 and containing 0.05% Tween 20. The ELISA-plate with the polypeptide M31 coated on the well surfaces were dried at 25° C. for 6 hours. The dried ELISA-plate were preserved at 4° C. for the next immunoassay.

EXAMPLE 3

Immnuoassay

<Preparation of Standard Samples>

100 μg/ml of polypeptide M31 were emulsified in an equivalent complete Freund's adjuvant to obtain an immunogen. 0.2 ml of this immunogen were subcutaneously injected into a New Zealand white rabbit of two weeks old to immunize the rabbit. A booster was performed one month after the first immunization and another booster was performed two months after the first immunization. Blood was collected from the immunized rabbit to obtain an antiserum three months after the first immunization. Diluted samples of ½ to 1/4096 of this antiserum were prepared, and these served as standard samples.

<Test Samples>

Following six types of test samples were prepared:

(a) 20 test samples (CHeAg) which were HBe antigen-positive and were collected from chronic hepatitis patients, (b) 20 test samples (CHeAb) which were anti-HBe antibody-positive and were collected from chronic hepatitis patients, (c) 20 test samples (ASCeAg) which were HBe antigen-positive and were collected from asymptomatic HBV-carriers, (d) 20 test samples (ASCeAb) which were anti-HBe antibody-positive and were collected from aysmptomatic HBV-carriers, (e) 20 test samples (LC) collected from hepatocirrhosis patients, and (f) 20 test samples (HCC) collected from hepatocellura caricinoma patients.

<Immunoassary>

The respective test samples were diluted to 100 times by a 0.01M PBS of pH7.0 containing a 0.01% BSA and 0.05% Tween 20. The diluted test samples were dispensed into wells of the ELISA-plate prepared in Example 2 and were reacted at 37° C. for 60 minutes. The reacted ELISA-plate were washed five times with a 0.01M PBS of pH7.0 containing 0.05% Tween 20. After the cleaning solution was removed, a 0.1-μg of peroxidase labeled anti-human IgG antibody was dispensed into the wells and were reacted therein at 37° C. for 60 minutes. After the reaction, the ELISA-plate was washed five times with a 0.01M PBS of pH7.0 containing 0.05% Tween 20.

After the cleaning solution was removed, a 0.1M citric acid-$Na_2HPO_4$ buffered solution containing 0.023hydrogen peroxide and 0.1 mg/ml of o- phyenylenediamine (OPD) was dispensed into the wells in an amount of 100 μl/well and was reacted at 37° C. for 30 minutes. After the reaction, 50μ of 5N sulfuric acid were added to the wells to stop the reaction. Absorbence (ABS) measurement was performed at a wavelength of 491 nm by using a plate reader.

TABLE 1

| Sample No. | ASCeAg-1 | ASCeAg-2 | ASCeAb-1 | ASCeAb-2 | CHeAg-1 | CHeAg-2 | CHeAb-1 | CHeAb-2 | LC-1 | LC-2 | HCC-1 | HCC-2 |
|---|---|---|---|---|---|---|---|---|---|---|---|---|
| 1 | 0.206 | 0.206 | 0.238 | 0.219 | 0.244 | 0.246 | 0.724 | 0.668 | 0.175 | 0.158 | 0.992 | 0.964 |
| 2 | 0.205 | 0.205 | 0.163 | 0.159 | 0.205 | 0.197 | 0.173 | 0.143 | 0.168 | 0.146 | 0.308 | 0.313 |
| 3 | 0.148 | 0.155 | 0.138 | 0.143 | 0.134 | 0.124 | 0.128 | 0.132 | 0.149 | 0.142 | 0.237 | 0.237 |
| 4 | 0.147 | 0.150 | 0.114 | 0.125 | 0.110 | 0.108 | 0.108 | 0.109 | 0.131 | 0.131 | 0.234 | 0.233 |
| 5 | 0.123 | 0.125 | 0.102 | 0.105 | 0.106 | 0.104 | 0.102 | 0.103 | 0.125 | 0.124 | 0.225 | 0.230 |
| 6 | 0.119 | 0.117 | 0.094 | 0.093 | 0.089 | 0.094 | 0.100 | 0.101 | 0.124 | 0.123 | 0.224 | 0.227 |
| 7 | 0.115 | 0.117 | 0.092 | 0.085 | 0.088 | 0.089 | 0.097 | 0.099 | 0.118 | 0.115 | 0.223 | 0.207 |
| 8 | 0.113 | 0.114 | 0.091 | 0.080 | 0.081 | 0.086 | 0.095 | 0.092 | 0.117 | 0.115 | 0.170 | 0.185 |
| 9 | 0.102 | 0.107 | 0.086 | 0.079 | 0.079 | 0.072 | 0.092 | 0.092 | 0.116 | 0.114 | 0.169 | 0.165 |
| 10 | 0.100 | 0.098 | 0.078 | 0.076 | 0.071 | 0.070 | 0.091 | 0.087 | 0.114 | 0.099 | 0.167 | 0.153 |
| 11 | 0.097 | 0.094 | 0.078 | 0.075 | 0.071 | 0.069 | 0.066 | 0.067 | 0.100 | 0.096 | 0.145 | 0.149 |
| 12 | 0.087 | 0.083 | 0.075 | 0.074 | 0.067 | 0.069 | 0.065 | 0.067 | 0.092 | 0.084 | 0.143 | 0.145 |
| 13 | 0.087 | 0.078 | 0.066 | 0.073 | 0.065 | 0.068 | 0.064 | 0.064 | 0.084 | 0.084 | 0.142 | 0.142 |
| 14 | 0.072 | 0.067 | 0.056 | 0.072 | 0.063 | 0.062 | 0.063 | 0.064 | 0.073 | 0.077 | 0.138 | 0.137 |
| 15 | 0.067 | 0.063 | 0.055 | 0.069 | 0.061 | 0.058 | 0.062 | 0.061 | 0.072 | 0.075 | 0.129 | 0.128 |
| 16 | 0.059 | 0.057 | 0.055 | 0.058 | 0.060 | 0.058 | 0.062 | 0.061 | 0.065 | 0.069 | 0.121 | 0.124 |
| 17 | 0.056 | 0.054 | 0.051 | 0.053 | 0.051 | 0.053 | 0.060 | 0.060 | 0.065 | 0.059 | 0.120 | 0.117 |
| 18 | 0.055 | 0.050 | 0.044 | 0.043 | 0.044 | 0.042 | 0.057 | 0.058 | 0.059 | 0.056 | 0.098 | 0.099 |
| 19 | 0.055 | 0.049 | 0.039 | 0.043 | 0.040 | 0.040 | 0.053 | 0.056 | 0.051 | 0.053 | 0.076 | 0.076 |
| 20 | 0.054 | 0.047 | 0.034 | 0.041 | 0.035 | 0.034 | 0.051 | 0.052 | 0.050 | 0.041 | 0.067 | 0.062 |
| Average Value | 0.103 | 0.102 | 0.087 | 0.088 | 0.088 | 0.087 | 0.116 | 0.112 | 0.102 | 0.098 | 0.206 | 0.205 |
| Maximum Value | 0.206 | 0.206 | 0.238 | 0.219 | 0.244 | 0.246 | 0.724 | 0.668 | 0.175 | 0.158 | 0.992 | 0.964 |
| Minimum Value | 0.054 | 0.047 | 0.034 | 0.041 | 0.035 | 0.034 | 0.051 | 0.052 | 0.050 | 0.041 | 0.067 | 0.062 |

Figure 5:
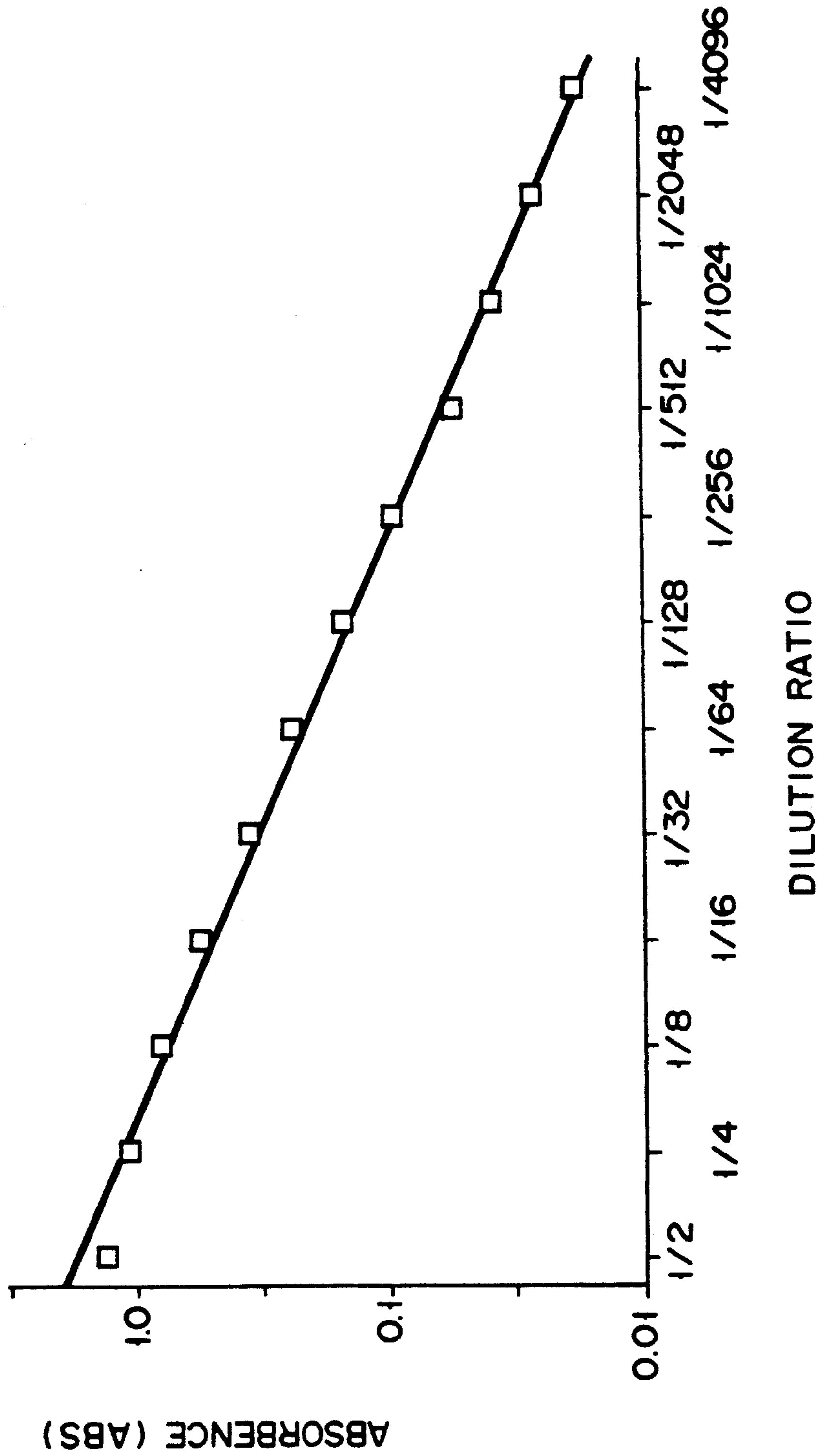
FIG. 5 is a graph showing a calibration curve showing a relationship between the dilution ratio and the absorbence of a standard sample in an immunoassay using the polypeptide M31.

Prior to the measurements of the test samples, similar measurements were performed for the standard samples to obtain a calibration curve representing the relationship between the dilution ratio and the absorbence. A measurement result is shown in FIG. 5. In FIG. 5, the dilution ratios are plotted along the abscissa and the absorbence values (ABS) are plotted along the ordinate.

The measurement results of the test samples are shown in Table 1 below. The immunoassay operations were performed twice for each test sample. Reference numerals suffixed to the test samples in Table 1 represent the first and second measurements. For example, ASCeAg-1 represents the first measurement result of the HBe antigen positive test samples collected from the asymptomatic HBV-carries.

In measurements of hepatocellular carcinoma test samples (HCC-1 and HCC-2), average measurement values are twice or more than those in other diseases, and a maximum value is about five times the average value. When an absorbence of 0.2 is given as a cutoff value, about 35% of the hepatocellular carcinoma patients were positive. The rates of positiveness for other samples in the immunoassay are as follows: 10% for ASCeAg; 5% for ASCeAb; 7.5% for CHeAg; 5% for CHeAb; and 0% for LC.

Judging from the above test results, the polypeptide according to the present invention is apparently effective in diagnosis of hepatocellular carcinoma and so on.

Additional advantages and modifications will readily occur to those skilled in the art. Therefore, the invention in its broader aspects is not limited to the specific details, and illustrated examples shown and described herein. Accordingly, various modifications may by without departing from the spirit or scope of the general inventive concept as defined by the appended claims and their equivalents.

What is claimed is:

1. A peptide having immunoreactivity with an antibody specific to hepatitis B virus, said peptide consisting essentially of at least six consecutive amino acids of the following amino acid sequence:

Asp-Cys-Val-Phe-Lys-Asp-Trp-Glu-Glu-Leu-Gly-
Glu-Glu-Ile-Arg-Leu-Lys-Val-Phe-Val-Leu-Gly-
Gly-Cys, said peptide not including the entire amino acid sequence of Protein X.

2. The peptide according to claim 1, wherein the peptide is immobilized on a surface of a support.

3. The immobilized peptide according to claim 2, wherein the support is selected from the group consisting of bovine serum albumin, an inner wall of a synthetic resin microplate, a latex bead having a diameter of 0.1 μm to 5.0 μm and a polystyrene bead having a diameter of 5 μm.

4. A peptide having immunoreactivity with an antibody specific to hepatitis B virus, said peptide consisting essentially of at least six continuous amino acids of the following amino acid sequence:

Asp-Cys-Val-Phe-Lys-Asp-Trp-Glu-Glu-Leu-Gly-
Glu-Glu-Ile-Arg-Leu-Met-Ile-Phe-Val-Leu-Gly-
Gly-Cys, said peptide not including the entire amino acid sequence of Protein X.

5. The peptide according to claim 4, wherein the peptide is immobilized on a surface of a support.

6. The immobilized peptide according to claim 5, wherein the support is selected from the group consisting of bovine serum albumin, an inner well wall of a synthetic resin microplate, a latex bead having a diameter of 0.1 μm to 5.0 μm and a polystyrene bead having a diameter of 5 mm.

7. A peptide having immunoreactivity with an antibody specific to hepatitis B virus, said peptide consisting essentially of at least six continuous amino acids of the following amino acid sequence:

Asp-Cys-Val-Phe-Lys-Asp-Trp-Glu-Glu-Leu-Gly-Glu-Glu-Ile-Arg-Leu-Lys-Val-Phe-Val-Leu-Gly-Gly-Cys, said peptide not including the entire amino acid sequence of Protein X.

8. The peptide according to claim 7, wherein the peptide is immobilized on a surface of a support.

9. The immobilized peptide according to claim 8, wherein the support is selected from the group consisting of bovine serum albumin, an inner well wall of a synthetic resin microplate, a latex bead having a diameter of 0.1 μm to 5.0 μm and a polystyrene bead having a diameter of 5 mm.

* * * * *